(12) United States Patent
Lippert et al.

(10) Patent No.: US 7,519,422 B2
(45) Date of Patent: Apr. 14, 2009

(54) ELECTROTHERAPY DEVICE

(75) Inventors: Michael Lippert, Ansbach (DE); Gerald Czygan, Buckenhof (DE)

(73) Assignee: Biotronik CRM Patent AG (CH)

( * ) Notice: Subject to any disclaimer, the term of this patent is extended or adjusted under 35 U.S.C. 154(b) by 702 days.

(21) Appl. No.: 11/104,275

(22) Filed: Apr. 12, 2005

(65) Prior Publication Data

US 2005/0240233 A1 Oct. 27, 2005

(30) Foreign Application Priority Data

Apr. 14, 2004 (DE) .................... 10 2004 018 783
Jul. 9, 2004 (DE) .................... 10 2004 034 337

(51) Int. Cl.
*A61N 1/362* (2006.01)

(52) U.S. Cl. ............................. 607/9; 607/17

(58) Field of Classification Search ............... 607/2, 607/9, 17–19, 28–29
See application file for complete search history.

(56) References Cited

U.S. PATENT DOCUMENTS

| 4,674,518 A | 6/1987 | Salo |
| 5,417,717 A | 5/1995 | Salo et al. |
| 6,788,970 B1* | 9/2004 | Park et al. .................. 607/17 |
| 7,096,064 B2* | 8/2006 | Deno et al. .................. 607/9 |

FOREIGN PATENT DOCUMENTS

| DE | 87 13 037 | 4/1988 |
| DE | 41 11 505 | 10/1992 |
| EP | 1 062 974 | 12/2000 |

* cited by examiner

*Primary Examiner*—George R Evanisko
*Assistant Examiner*—Rex Holmes
(74) *Attorney, Agent, or Firm*—Hahn Loeser & Parks LLP

(57) ABSTRACT

Certain embodiments of the present invention disclose an implantable electrotherapy device comprising a housing in which are arranged an activity sensor, an impedance or conductivity measuring unit and an evaluation unit, wherein the evaluation unit is connected to the impedance or conductivity measuring unit and to the activity sensor and is adapted to evaluate the impedance or conductivity signal produced by the impedance or conductivity measuring unit and the respectively time-associated activity level signal and for producing and outputting a contractility signal, in such a way that the contractility signal is derived from the impedance or conductivity signal and the activity level signal and reflects the respective contractile state of a heart associated with an activity level signal value.

22 Claims, 3 Drawing Sheets

ELECTROTHERAPY DEVICE

CROSS-REFERENCE TO RELATED APPLICATIONS/INCORPORATION BY REFERENCE

This application claims priority to German patent application serial number 10 2004 018 783.5 filed on Apr. 14, 2004, which is incorporated herein by reference in its entirety. This application also claims priority to German patent application serial number 10 2004 034 337.3 filed on Jul. 9, 2004, which is incorporated herein by reference in its entirety.

TECHNICAL FIELD

Embodiments of the present invention relate to an electrotherapy device. In particular, certain embodiments of the present invention concern an implantable electrotherapy device such as, for example, a cardiac pacemaker or a defibrillator.

BACKGROUND OF THE INVENTION

Electrotherapy devices which can ascertain the contractility of a heart afford the possibility of adapting a therapy to be delivered by the electrotherapy device to the respective contractility state of the heart of the patient.

Contractility describes an inotropic state of the heart. It influences the force and the speed of a myocardiac contraction. Contractility is controlled by three mechanisms:
- direct control by the autonomous nervous system (ANS),
- the so-called Starling mechanism, and
- the so-called Bowditch effect (force-frequency coupling).

The main mechanism, control of circulatory regulation by the autonomous nervous system, increases contractility and heart rate when there is an increased metabolic demand, for example in the case of bodily or physical effort, in order to ensure a suitable blood supply.

In the case of patients with chronic heart failure (HF), myocardiac contractility decreases to a low level and interventricular synchronization is worsened. That is accompanied by a low ejection fraction (EF), as well as a low quality of life and a high mortality rate. HF occurs frequently in the population. HF patients are treated with various drugs which influence the inotropic state, for example betablockers, in order to stabilize the heart rate, but also with positive inotropic drugs, for example glycosides, in order to increase contractility. In more recent times HF patients are treated with resynchronization therapy devices, for example 3-chamber cardiac pacemakers or defibrillators. The aim of such pacemaker therapy is to synchronize the two ventricles of a heart by biventricular stimulation in order to improve the temporal performance of the chambers of the heart and thus heart efficiency (cardiac resynchronization therapy or CRT).

Contractility is therefore an important parameter to be observed, in particular for HF patients. Such observation is important in order
- to observe the state of the patient and an alleviation or progress in the disease,
- to establish and observe resynchronisation therapy of the heart (cardiac resynchronisation therapy or CRT), and
- to observe drug treatment.

Information about contractility can also be used to optimize cardiac pacemaker therapy or a therapy implemented by means of an implantable cardioverter/defibrillator (ICD).

Although the contractility is a parameter of great importance, it is difficult to measure in clinical practice. It is usual for contractility to be determined on the basis of a maximum ventricular pressure gradient $dp/dt_{max}$ in the right ventricle or in the left ventricle. A left-ventricular ejection fraction can also be determined by means of electrocardiography. An investigation of the right ventricle by means of electrocardiography is very difficult for anatomical reasons, although the information about the right ventricle is highly important for a complete investigation. Both procedures, pressure measurement and electrocardiography, are time-consuming and expensive. Ventricular pressure measurement requires an invasive intervention. It requires a pressure catheter in one or both ventricles and can only be implemented during an electrophysiological study or implantation of a cardiac pacemaker or cardioverter/defibrillator.

Implants with which the contractility of a heart can be ascertained are described, for example, in U.S. Pat. Nos. 4,674,518 and 5,417,717. In those cases measurement of the change in the heart chamber volume is effected by means of the pressure gradient dP/dt and by means of impedance plethysmography.

European patent application No 1 062 974 describes a cardiac pacemaker of the kind set forth in the opening part of this specification. The aim is for the control method described therein for an electrotherapy device and the electrotherapy device disclosed therewith to be further developed to expand the range of use of the electrotherapy device.

SUMMARY OF THE INVENTION

In accordance with certain embodiments of the present invention, the electrotherapy device has an activity sensor for detecting a physical activity and producing a corresponding activity level signal. A housing of the electrotherapy device is provided with an electrode line connection for the connection of at least one electrode line which is to be placed intracardially. The housing itself or a part of the housing can serve as a neutral electrode or reference electrode. The electrode line connection serves for connection to the electrode line which has at least one measuring electrode for recording an intracardiac impedance or conductivity signal. Arranged in the housing is an impedance or conductivity measuring unit adapted to produce a unipolar or bipolar impedance or conductivity pattern signal. For that purpose, a plurality of impedance or conductivity values or a corresponding impedance or conductivity pattern are measured during at least one cardiac cycle. Such is effected either in unipolar mode by measurement between a neutral electrode and a measuring electrode or between two measuring electrodes. Also arranged in the housing is an evaluation unit which serves for evaluating the impedance or conductivity pattern and for deriving a contractility value from the impedance or conductivity pattern.

In accordance with an embodiment of the present invention, an electrotherapy device of the kind set forth in the opening part of this specification is provided, whose evaluation unit is adapted for evaluating the impedance or conductivity pattern signal produced by the impedance or conductivity measuring unit and for producing and delivering a contractility difference signal in dependence on the impedance or conductivity pattern signal and the respectively time-associated activity level signal and for producing and delivering a contractility signal, in such a way that the contractility signal is derived from the impedance or conductivity signal and the activity level signal and reflects the respective contractile state of a heart associated with an activity level signal value.

In accordance with an embodiment of the present invention, the evaluation unit is adapted to evaluate the impedance or conductivity pattern signal produced by the impedance or conductivity measuring unit and to produce and deliver a contractility difference signal in dependence on the impedance or conductivity pattern signal by forming a difference between two impedance or conductivity pattern signals at different periods of time, in such a way that a respective contractility difference value of the contractility difference signal depends on an area which two impedance or conductivity pattern signals detected at different periods of time enclose between them. The evaluation unit is further adapted to associate with a respective contractility difference value determined in that way, an activity signal value which applies in respect of at least one of the periods of time in which the impedance or conductivity pattern signals which contributed to forming the respective contractility difference value were recorded.

In that respect, the area enclosed by two impedance or conductivity pattern signals detected at different periods of time can be a notional area which would be afforded upon graphic representation of the impedance patterns.

That area is moreover already described in EP 1 062 974 but without reference to periods of time to be associated with the conductivity patterns illustrated therein and without the corresponding automatic association of activity values. That association makes it possible to associate a contractility difference which is possibly present or not present with an activity difference which is present or not present.

Instead of a measurement of the impedance pattern, it is also possible to measure the pattern of the reciprocal of the impedance, that is to say the pattern of conductivity, see EP 1 062 974.

If, similarly as already described in EP 1 062 974, a conductivity or impedance pattern signal is stored for a known activity signal (for example recorded in the rest condition of the patient) and if that stored impedance pattern signal is regularly used for difference formation with a further impedance pattern signal, it is basically sufficient if the stored activity signal reflects the activity during the period of time at which the further impedance pattern signal was recorded.

It is however desirable to entirely forego storage of a reference impedance signal pattern which has once been predetermined. Instead, a reference signal pattern is to be formed from the outset in dependence on simultaneously recorded activity level signal values. In accordance with an embodiment of the present invention, that is effected by a procedure whereby only those impedance or conductivity signal patterns which involve activity level values below a predetermined limit activity level value are used for forming an averaged reference signal pattern. The impedance or conductivity signal patterns which are used in that way for forming a reference signal pattern, in a particular embodiment, are firstly standardized with the respective time-associated activity level value, before the impedance or conductivity signal patterns which are standardized in that way are then averaged to form the reference signal pattern. In addition to standardization of a contractility signal (calculated from the impedance pattern) itself with the activity, it is also possible to effect standardization of the contractility difference signal (differential area between current and reference impedance pattern) with the activity level signal value difference. That involves the production of a contractility difference signal which is standardized to the activity difference and which is a measurement in respect of the capability of the heart to also increase contractility (measured by way of the impedance pattern) with rising load (measured in the form of physical activity).

In accordance with an embodiment of the present invention, the periods of time over which the respective impedance pattern signals are to be recorded involve the duration of at least one defined part of a cardiac cycle or an entire cardiac cycle or an integral number of few cardiac cycles, that is to say not 100 cardiac cycles but for example only 8 or 16 cardiac cycles.

In accordance with an embodiment of the present invention, the electrotherapy device is further adapted to form a respective impedance pattern signal by means of unipolar impedance measurement, in which measurement is effected between a neutral electrode arranged at the housing of the electrotherapy device and a measuring electrode in the heart.

In accordance with an embodiment of the present invention, the impedance or conductivity measuring unit has an input amplifier with an automatic input gain control (AGC) so that the output signal of an impedance or conductivity sensor is in each case matched in as optimum a fashion as possible to a subsequent analog-digital converter. In that case the impedance or conductivity measuring unit is adapted to scale the respective amplified output signal of the input amplifier, after analog-digital conversion thereof, with the associated gain factor.

An advantageous variant of an implantable electrotherapy device in the form of a cardiac pacemaker or defibrillator is afforded if there is provided in the housing of the therapy device a therapy device control unit which is connected to the evaluation unit and sets at least one therapy parameter such as univentricular or biventricular stimulation, interventricular delay time, atrio-ventricular delay time in dependence on a respective contractility signal or a contractility difference signal. In that respect the therapy device control unit is, in accordance with an embodiment of the present invention, designed in such a way that it automatically sets the respective therapy parameter so that the contractility signal or the contractility difference signal indicates maximum contractility.

In accordance with an embodiment of the present invention, provided in the housing is a data memory for the contractility signal and additionally for the activity level signal. That data memory is also referred to hereinafter as the memory and makes it possible to store both the conductivity or impedance signal patterns required for calculation of the contractility difference signal and also the pattern of the respective contractility difference signal itself in order for same to be capable of being called up telemetrically, in accordance with an embodiment of the present invention.

In accordance with an embodiment of the present invention, the data memory includes a plurality of memory regions which serve for separate storage, for example, of a reference signal pattern and at least one prevailing impedance or conductivity signal pattern and a contractility signal pattern or contractility difference signal pattern and the associated activity level signal pattern. The memory regions referred to here contain data relating to different time ranges: the data relating to the reference signal pattern and to the impedance signal pattern typically concern a period of time of less than one cardiac cycle while the data relating to the contractility signal pattern or the contractility difference signal pattern and the activity level signal pattern respectively concern a period of time of up to several months.

In accordance with an embodiment of the present invention, the data memory is connected to the therapy control unit. In addition the data memory is connected to the evaluation unit.

In accordance with an embodiment of the present invention, disposed in the housing is a data telemetry unit which is connected to the therapy control unit or to the data memory or both.

BRIEF DESCRIPTION OF SEVERAL VIEWS OF THE DRAWINGS

The invention will now be described in greater detail by means of an embodiment with reference to the Figures in which.

DETAILED DESCRIPTION OF THE INVENTION

Figure 1:
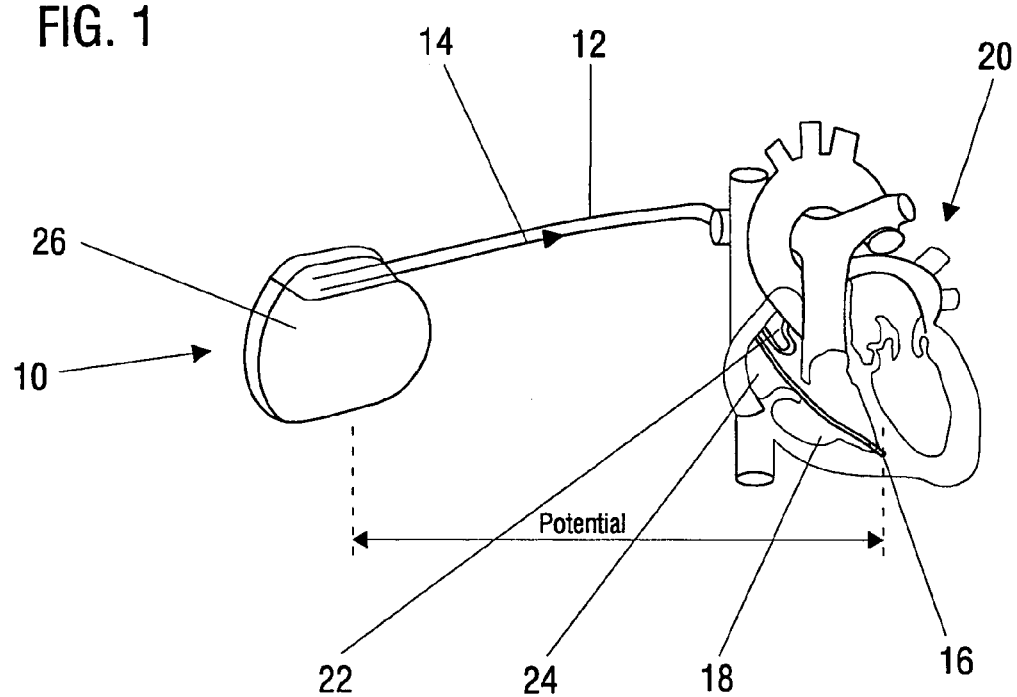
FIG. 1 is a diagrammatic view of an implantable therapy device in the form of a cardiac pacemaker and an associated electrode line and a heart, in accordance with an embodiment of the present invention.

The arrangement in FIG. 1 includes a cardiac pacemaker 10 to which two electrode lines are connected, more specifically an atrial electrode line 12 and a ventricular electrode line 14. The ventricular electrode line 14 has a tip electrode 16 which is placed at the apex of a right heart chamber 18 of a diagrammatically illustrated heart 20. In the region of its distal end the atrial electrode line 12 is bent in a j-shaped configuration and has an atrial tip electrode 22 arranged in the right atrium 24 of the heart 20.

Figure 4:
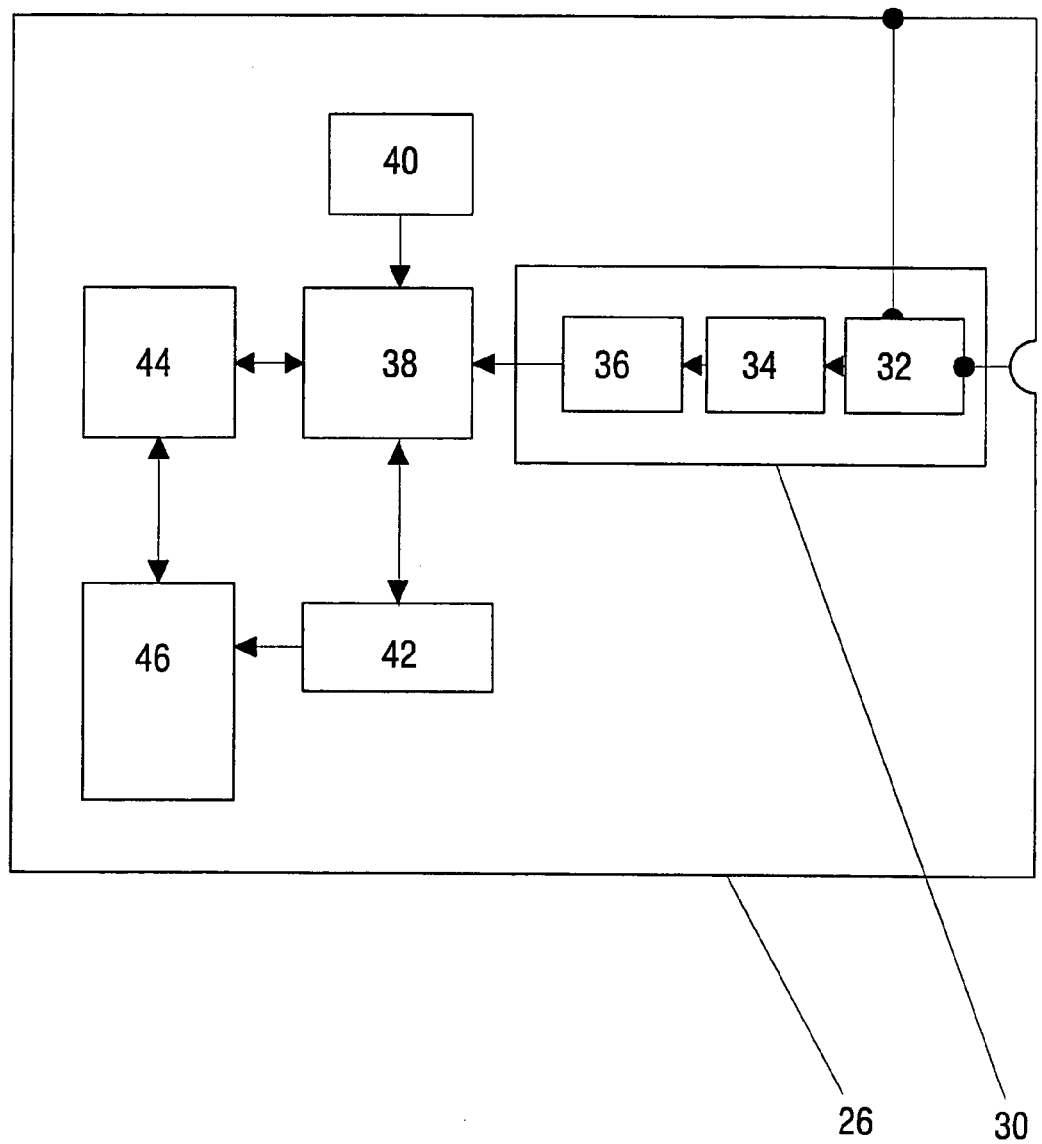
FIG. 4 shows a schematic block circuit diagram of the implantable therapy device of FIG. 1, in accordance with an embodiment of the present invention.

To record the impedance configuration which is of interest here the impedance between the ventricular tip electrode 16 and a neutral electrode formed by a housing 26 of the pacemaker 10 is measured. For that purpose the neutral electrode 26 and the ventricular tip electrode 16 are connected to an input amplifier 34 which is arranged in the interior of the housing 26 and which is diagrammatically illustrated in FIG. 4.

That input amplifier 34 has automatic gain control which provides that an impedance signal measured between the neutral electrode 26 and the ventricular tip electrode 16 is amplified with a variable gain factor. Automatic gain control (AGC) provides that the output signal of an impedance sensor is matched in the best possible fashion to a downstream-connected analog-digital converter 36. The impedance sensor 32, the filter with the input amplifier 34 and the analog-digital converter 36 are a component part of an impedance measuring unit 30 which as its output signal delivers an impedance pattern signal which is scaled with the respectively set gain factor. That impedance pattern signal can be a quasi-continuous signal or an impedance signal which is time-sampled at relatively great time intervals and which is sampled by means of a sample-and-hold circuit. Automatic gain control serves for optimum matching of the impedance sensor output signal to the AD converter.

Also arranged in the interior of the housing 26 of the cardiac pacemaker 10 is an activity sensor 40 which is suitable for detecting a respective activity level of a patient and producing a corresponding activity level signal. In accordance with an embodiment of the present invention, the activity sensor 40 is an accelerometer and accordingly measures the respective acceleration of the cardiac pacemaker 10.

Connected downstream of the impedance unit 30 and the activity sensor 40 is an evaluation unit 38 which is also disposed in the housing 26.

Also arranged in the housing 26 of the cardiac pacemaker 10 is an impedance pattern memory 42 which is connected at least indirectly to the evaluation unit 38 and can be connected directly to the impedance measuring unit 30.

The evaluation unit 38 is adapted to form a contractility or contractility difference signal from two impedance pattern signals detected at periods of time which are different but of equal length. For that purpose the contractility difference signal is formed in such a way that it approximately corresponds to an area included between two impedance pattern signals (see FIG. 3, differential area DA). The operation of determining that contractility difference signal is effected, in accordance with an embodiment of the present invention, by a procedure whereby firstly a reference zero time is ascertained for the two impedance pattern signals, for example being given by a respective R blip. Then, for a series of successive time intervals from the reference zero time, the respective absolute value in respect of the difference of the two impedance pattern signals is formed and finally the sum of those absolute difference values over the different intervals of time is formed. That affords a contractility difference value corresponding to the sum of the absolute values of the area integrals of the areas included by the two impedance pattern signals.

Figure 2:
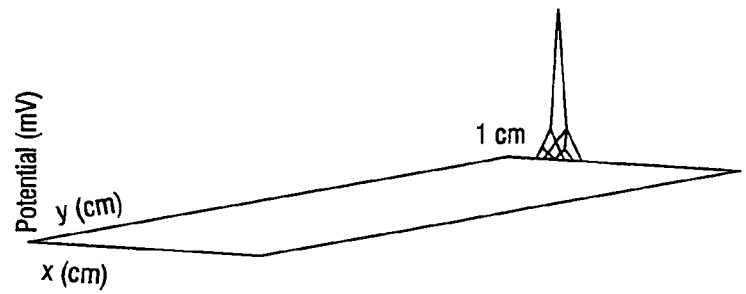
FIG. 2 shows a simulated potential distribution for an arrangement as shown in FIG. 1, in accordance with an embodiment of the present invention.

As described hereinbefore, a respective impedance pattern is measured in unipolar mode. As FIG. 2 shows such an impedance pattern measured in unipolar mode at the apex of a chamber of the heart substantially reflects the pattern of the local impedance around the measuring electrode (ventricular tip electrode).

The claimed device is based on observation of ventricular contractility by means of an implanted cardiac pacemaker or cardioverter/defibrillator by means of intracardiac impedance measurement. Calculation of an electromagnetic field, as is shown in FIG. 2, shows that an impedance value measured in unipolar mode by means of a measuring electrode arranged at the tip of the chamber of the heart reflects impedance changes in the close proximity around the measuring electrode.

The measured impedance signal changes during the contraction of the heart because blood and the myocardium tissue involve different levels of electrical conductivity. Therefore, the time configuration in respect of the impedance which is measured in unipolar mode reproduces the contraction dynamics of the ventricular apex. It is known that the right-ventricular impedance signal measured by a unipolar procedure coincides well with the maximum of the change in pressure in the right ventricle during a cardiac cycle.

Impedance measurement itself is known per se. A constant, pulsed current is fed in between two electrodes and the voltage resulting therefrom is time-sampled, filtered, amplified and subjected to analog-digital conversion.

In principle all available electrodes can be used as the electrodes for feeding in the current and as voltage-measuring electrodes. That applies in particular to arrangements in which there are more electrodes than in the arrangement illustrated in FIG. 1. In that respect the same electrodes can be used both for feeding in the current and also for measuring the voltage. In accordance with the embodiment shown in FIG. 1, the voltage is measured in unipolar mode between the cardiac pacemaker housing 26 and the ventricular tip electrode 16 and the measurement current is also fed in between those two electrodes. Instead of the right-ventricular tip electrode, it is also possible for a left-ventricular electrode arranged for example in the coronary sinus or a lateral vein branching therefrom to serve as the measuring electrode. The contractility signal which has already been referred to above is derived from the impedance pattern signal obtained in that way, more specifically, in accordance with an embodiment of the present invention, in the form of a contractility difference signal which is obtained by comparing an impedance signal pattern in the rest condition of the patient and an impedance signal pattern in the load condition of the patient.

Figure 3:
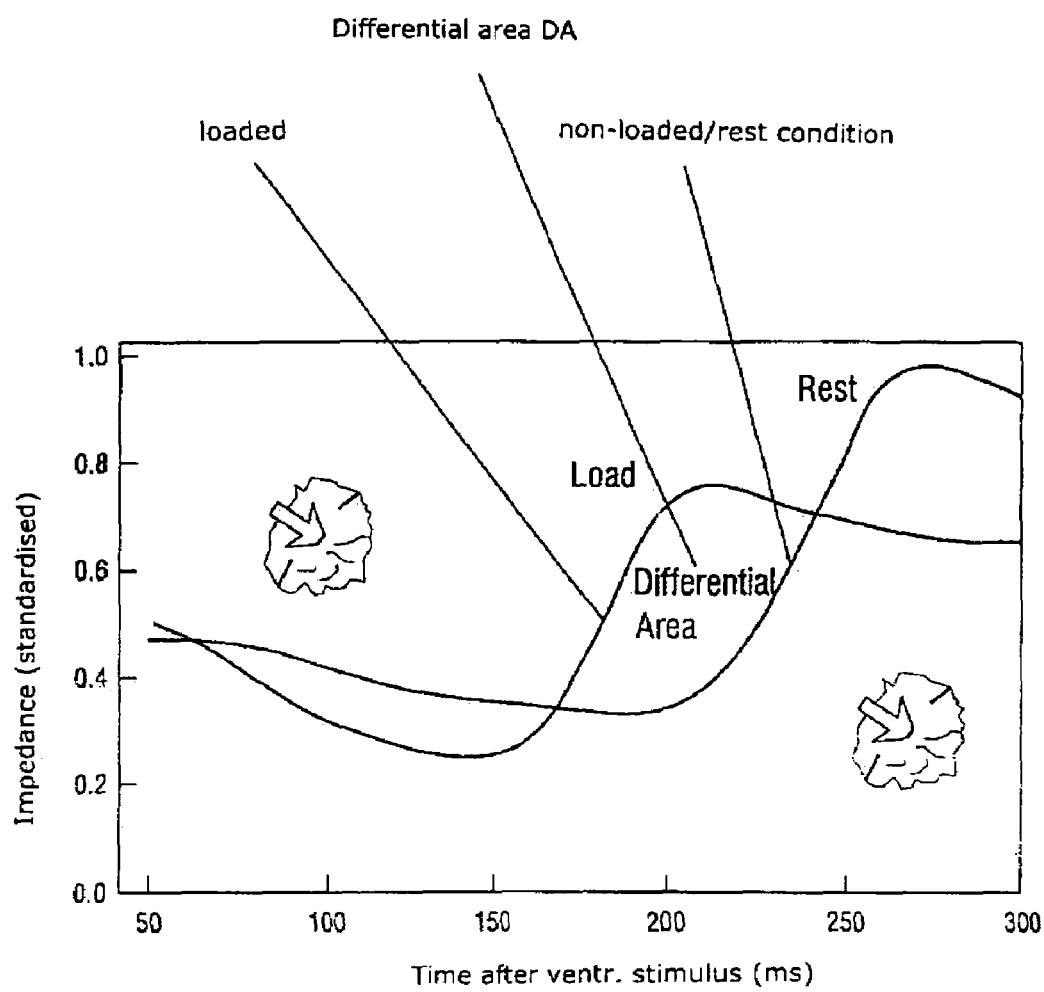
FIG. 3 shows impedance pattern signals recorded with the arrangement of FIG. 1 for a non-loaded and a loaded state together with the illustration of a differential area, in accordance with an embodiment of the present invention.

As already mentioned previously, the contractility difference signal is formed, in accordance with an embodiment of the present invention, in such a way that it reflects the differential area which is included by two impedance pattern signals recorded at different moments in time. Impedance pattern signals for a rest condition and a load condition are shown in FIG. 3. In addition, FIG. 3 illustrates the differential area included by those two impedance pattern signals.

As already stated, the differential area is the absolute difference between the impedance pattern signal for the rest condition of the patient and the impedance pattern signal for the stressed condition of the patient. The differential area DA can be calculated as follows for two impedance pattern signals with N sample values in each case, for which there is in each case a load impedance value $Z_{bel}$ (or acute impedance value $Z_{akut}$) and a rest impedance value $Z_{Ruhe}$ (or reference impedance value $Z_{Ref}$):

$$DA = \frac{1}{N}\sum_{i=1}^{N} |Z_{akut}(i) - Z_{Ref}(i)|$$

The two impedance pattern signals or their sample indices i are in that case related to a suitable reference zero time, for example in each case the R-blip in the associated electrocardiogram.

Instead of a rest impedance pattern with rest impedance values $Z_{Ruhe}$ and a load impedance pattern with impedance values $Z_{bel}$ it is also possible to use any reference impedance pattern as the reference signal with impedance values $Z_{Ref}$ and a respectively prevailing impedance signal pattern with impedance values $Z_{akut}$.

Impedance is continuously measured in each case, for example at each heartbeat. The prevailing impedance pattern is formed as a short-term average value with a small time constant, for example a 15/16 recursive low pass filter. The reference impedance pattern is preferably an averaged rest impedance signal pattern which is formed only from those impedance signal patterns which were recorded in the rest condition of the patient. That reference impedance pattern is filtered with a long time constant, for example with a 255/256 recursive low pass filter.

Whether a patient is in the rest condition or in the load condition is determined on the basis of the output signal from the activity sensor, that is to say the accelerometer. That accelerometer outputs an activity level signal which indicates whether the patient is resting or is physically active. A motional flag Mflag can be derived from the activity level signal, the motional flag being set (Mflag=1) when an output signal of the accelerometer exceeds a predetermined limit value. The motional flat Mflag is reset (Mflag=0) when the output signal of the accelerometer falls short of a predetermined second limit value. The first and second limit values can be different but can also be identical. The reference impedance pattern signal is formed only when the motional flag is reset (Mflag=0).

The Mflag serves for controlling averaging of the reference impedance signal pattern. It is not intended to replace the activity level signal as (for example for standardization of the contractility reference signal) the activity level signal is intended to be able to reproduce a plurality of steps in the activity level.

If in the load situation of the patient the first limit value is exceeded and the Mflag is set (Mflag=1), formation of the reference impedance pattern signal is interrupted. At the same time an average differential area $DA_{avg}$ is calculated. That average differential area is determined for a predetermined, for example programmable observation period, for example 24 hours. With the commencement of each new observation period, a fresh average differential area $DA_{avg}$ is calculated.

In addition to calculation of the average differential area $DA_{avg}$, it is also possible to ascertain an average activity level signal. Each average differential area (that is to say each average contractility difference signal) can then be standardized with the respectively associated activity level signal value.

Alternatively the average differential area $DA_{avg}$ (the average contractility difference signal value) can be calculated for various output value ranges of the accelerometer. In addition it is possible for a respective contractility difference signal value (the differential area) to be standardized with a respectively associated, short-term averaged activity level signal value before the averaged differential area, that is to say the averaged contractility difference signal value, is formed. That standardization operation ensures that observation periods with different activity levels are comparable.

The impedance pattern to be measured does not depend solely on the contraction dynamics which are influenced by contractility, but also on the nature of the ventricular event, that is to say whether the ventricular contraction is a natural contraction or a stimulated contraction. The impedance pattern (and the contraction pattern) can be different in the case of stimulated contractions and in the case of intrinsic, natural ventricular contractions. Therefore, in accordance with an embodiment of the present invention, the average differential area $DA_{avg}$ is calculated separately for the two different kinds of ventricular events (stimulated and intrinsic).

For that purpose, in accordance with an embodiment of the present invention, the evaluation unit and a therapy control unit 44 which controls for example the delivery of stimulation pulses are connected together at least indirectly in such a way that the therapy control unit 44 delivers a signal to the evaluation unit 38 when a ventricular stimulation takes place. In accordance with an embodiment of the present invention, that signal is a per se known marker signal for characterizing ventricular stimulation.

The average differential area $DA_{avg}$ which is determined in that way is an indicator in respect of the average change in contractility during a physical load on an individual patient. That value can be used for diagnostic and therapeutic purposes in the manner described hereinafter.

Basically it is also possible for a signal characterizing contractility to be obtained from the impedance signal in a different fashion, thus as is the case for example in the above-quoted state of the art (for example by impedance plethysmography or by forming the second derivative of the impedance signal). Distinguishing between the rest condition and a load condition of a patient like also the averaging operation over a predetermined period of time should also be effected in such cases (determining the contractility from the impedance in a different manner than by way of the differential area) as described herein.

In accordance with an embodiment of the present invention, the cardiac pacemaker 16 includes a therapy control unit 44 which is adapted to set one or more stimulation parameters to be controlled thereby such as the stimulation mode—biventricular, right-ventricular, left-ventricular etc—an atrio-ventricular delay time or an interventricular delay time, in dependence on the respective contractility signal, in such a way as to afford a respective maximum level of contractility. In that respect, that optimization of the stimulation parameters by the therapy control unit 44 is, in accordance with an embodiment of the present invention, effected in the manner of regulation in a recursive fashion, by a procedure whereby an initially predetermined stimulation parameter (for example, for the atrio-ventricular delay time or the interventricular delay time) is altered stepwise and that value of the control parameter for which the respective highest degree of contractility was afforded is always used as the starting point for the next change. Along those lines, the therapy control unit 44 accesses a memory 42 for the contractility signal which in accordance with an embodiment of the present invention, is given by the configuration of the average differential area $DA_{avg}$.

That therapy control unit 44 can additionally be connected to the evaluation unit 38 in the above-mentioned value in such a way that the evaluation unit receives a marker signal when ventricular stimulation takes place.

In accordance with another embodiment of the present invention, the memory 42 for the contractility signal has separate memory regions for the differential area $DA_{avg}$, for both kinds of ventricular events and for the number of differential area values which have contributed to the formation of the respective differential area $DA_{avg}$. That memory is, in accordance with an embodiment of the present invention, connected to a telemetry unit 46 so that the values stored in the memory 42 can be telemetrically interrogated by a physician.

Besides memory regions for the last-mentioned data in respect of the contractility signal (the differential area) there is provided, in accordance with an embodiment of the present invention, a further memory region for the associated activity level signal values. The data which are to be telemetrically interrogated by the physician in that way can then be graphically represented on a display screen and can assist with diagnosis by the physician.

The averaged contractility and activity level signals can also be communicated in the context of so-called home monitoring on a regular, for example daily, basis, to an external device, by means of the telemetric link of the cardiac pacemaker 16. In that case the data transmitted to an external device are communicated from that external device to a central service center in per se known manner and can be correlated with the data which are already previously stored there.

The therapy control unit can also be designed in such a way that it triggers data transmission of its own accord when there is a particular event, for example an alarm condition. That particular event can be for example a detected arrhythmia. It is equally possible for the particular event to be a telemetrically received request on the part of a physician or the patient himself. In connection with monitoring and evaluation of the contractility signal, a particular event triggering a telemetric connection can also be a significant change in the contractility signal, that is to say, in accordance with an embodiment of the present invention, of the value of the differential area itself.

Observation of the contractility which is ascertained by means of an implanted electrotherapy device, in the above-described manner, can be used for various diagnostic or therapeutic purposes. The diagnostic options include:

general monitoring of patients with heart failure (HF patients) by means of the stored and telemetrically transmitted data, monitoring of the HF patients by means of the home monitoring data and the above-mentioned alarm functionality, monitoring of a drug, for example if drugs with positive or negative inotropic action are being administered, monitoring of a resynchronisation therapy, and/or observation of patients who exhibit an increased risk of sudden changes in contractility, for example patients with the risk of a myocardial infarction or an ischemia.

The therapeutic options are as follows:

adaptation of the stimulation mode to detected changes in contractility, for example switching over between right-ventricular, left-ventricular and biventricular stimulation, and adaptation of other stimulation or defibrillation parameters, for example such time parameters as the above-mentioned atrio-ventricular delay time, the biventricular delay time but also the stimulation rate itself, or additionally or alternatively adaptation or control of a drug therapy by the physician.

In addition, such a cardiac pacemaker can also be used as an acute sensor, for example during an electrophysiological investigation, if the patient has permanently implanted electrode lines. The reaction of the heart to a temporary use of a positively inotropic medicament, for example dobutamine, or to a standardized load, can also be tested. Various investigations on a patient can be compared together and the changes in the respective load reaction can be evaluated. That use serves for the diagnosis of cardiac insufficiency, regular observation of a worsening or improvement in cardiac defects and for testing general contractility.

What is claimed is:

1. An implantable electrotherapy device comprising:

a housing which has an electrode line connection for the connection of at least one electrode line which is to be placed intracardially and which has at least one measuring electrode for recording an intracardiac impedance signal;

an activity sensor, arranged in the housing, which is adapted to produce an activity level signal whose respective activity level signal values in the implanted condition of the therapy device depend on a physical activity of a patient;

an impedance or conductivity measuring unit, arranged in the housing, which is adapted to produce a unipolar or bipolar impedance or conductivity signal by measuring an impedance or conductivity value between a neutral electrode and a measuring electrode or between two measuring electrodes; and an evaluation unit, arranged in the housing, wherein the evaluation unit is connected to the impedance or conductivity measuring unit and the activity sensor and is adapted for evaluating the impedance or conductivity pattern signal produced by the impedance or conductivity measuring unit and the respectively time-associated activity level signal and for producing and delivering a contractility signal, in such a way that the contractility signal is derived from the impedance or conductivity signal and the activity level signal and reflects the respective contractile state of a heart associated with an activity level signal value, wherein the electrotherapy device is adapted to produce a respective time-sampled impedance or conductivity pattern signal and a time-sampled activity level signal associated in respect of time with the respective impedance or conductivity pattern signal, and wherein the evaluation unit is adapted to form a reference signal pattern from at least one impedance or conductivity pattern signal in dependence on simultaneously recorded activity level signal values, and wherein the evaluation unit is further adapted to standardize the contractility signal or a contractility signal difference pattern with a respective time-associated activity level signal value or an activity level signal value difference.

2. The electrotherapy device as set forth in claim 1, wherein the housing includes a neutral electrode and the impedance or conductivity measuring unit is adapted to produce a unipolar impedance or conductivity signal by measuring an impedance or conductivity value between a neutral electrode and a measuring electrode and that the evaluation unit is adapted to derive the contractility signal from the unipolar impedance or conductivity signal.

3. The electrotherapy device as set forth in claim 2, wherein the evaluation unit is adapted to evaluate the contractility signal as a contractility difference signal in dependence on the impedance or conductivity pattern signal by forming a difference between two impedance or conductivity pattern signals recorded in different periods of time, in such a way that a respective contractility difference value of the contractility difference signal depends on an area which the two impedance or conductivity pattern signals detected at different periods of time include between them.

4. The electrotherapy device as set forth in claim 3, wherein the evaluation unit is adapted to associate with a respective contractility difference value an activity level signal value which applies for at least one period of time which is associated with at least one of the impedance or conductivity pattern signals.

5. The electrotherapy device as set forth in claim 1, wherein the evaluation unit is adapted to form the reference signal pattern by averaging of a plurality of impedance or conductivity signal patterns.

6. The electrotherapy device as set forth in claim 5, wherein the evaluation unit is adapted, for forming the reference signal pattern by averaging, to take account only of those impedance or conductivity signal patterns with each of which there is associated in respect of time a respective activity level signal value below a predetermined limit activity level value.

7. The electrotherapy device as set forth in claim 6, wherein the electrotherapy device is designed in such a way that a respective period of time over which a respective impedance or conductivity pattern signal is to be recorded or formed is the duration of at least a defined portion of a cardiac cycle or a whole cardiac cycle or an integral number of a few cardiac cycles.

8. The electrotherapy device as set forth in claim 2, wherein the electrotherapy device is designed in such a way that a respective period of time over which a respective impedance or conductivity pattern signal is to be recorded or formed is the duration of at least a defined portion of a cardiac cycle or a whole cardiac cycle or an integral number of a few cardiac cycles.

9. The electrotherapy device as set forth in claim 7, wherein the impedance or conductivity measuring unit has an input amplifier with automatic input gain control (AGC) so that the respective gain of an output signal of an impedance or conductivity sensor of the impedance or conductivity measuring unit is as optimum as possible, wherein the impedance or conductivity measuring unit is adapted to scale an output signal of the input amplifier with a respectively associated gain factor.

10. The electrotherapy device as set forth in claim 1, wherein the impedance or conductivity measuring unit has an input amplifier with automatic input gain control (AGC) so that the respective gain of an output signal of an impedance or conductivity sensor of the impedance or conductivity measuring unit is as optimum as possible, wherein the impedance or conductivity measuring unit is adapted to scale an output signal of the input amplifier with a respectively associated gain factor.

11. The electrotherapy device as set forth in claim 9, wherein provided in the housing is a therapy device control unit which is connected to the evaluation unit and is adapted to set at least one therapy parameter such as univentricular or biventricular stimulation, interventricular delay time, atrioventricular delay time in dependence on a respective contractility signal or a contractility difference signal.

12. The electrotherapy device as set forth in claim 1, wherein provided in the housing is a therapy device control unit which is connected to the evaluation unit and is adapted to set at least one therapy parameter such as univentricular or biventricular stimulation, interventricular delay time, atrioventricular delay time in dependence on a respective contractility signal or a contractility difference signal.

13. The electrotherapy device as set forth in claim 11, wherein the therapy device control unit is adapted to set the respective therapy parameter in such a way that the contractility signal or the contractility difference signal exhibits maximum contractility.

14. The electrotherapy device as set forth in claim 13, wherein provided in the housing is a data memory for the contractility signal and preferably additionally for the activity level signal.

15. The electrotherapy device as set forth in claim 1, wherein provided in the housing is a data memory for the contractility signal and preferably additionally for the activity level signal.

16. The electrotherapy device as set forth in claim 11, wherein the data memory has a plurality of memory regions for a reference signal pattern and for at least one prevailing impedance or conductivity signal pattern as well as for a respectively associated activity level signal pattern.

17. The electrotherapy device as set forth in claim 16, wherein the data memory is connected to the therapy control unit.

18. The electrotherapy device as set forth in claim 11, wherein the data memory is connected to the therapy control unit.

19. The electrotherapy device as set forth in claim 17, wherein the data memory is connected to the evaluation unit.

20. The electrotherapy device as set forth in claim 11, wherein the data memory is connected to the evaluation unit.

21. The electrotherapy device as set forth in claim 19, wherein arranged in the housing is a data telemetry unit which is connected to the therapy control unit or the data memory or both.

22. The electrotherapy device as set forth in claim 11, wherein arranged in the housing is a data telemetry unit which is connected to the therapy control unit or the data memory or both.

* * * * *